US010575866B2

(12) United States Patent
Jezierski et al.

(10) Patent No.: US 10,575,866 B2
(45) Date of Patent: Mar. 3, 2020

(54) REUSABLE BLADE HUB ASSEMBLY

(71) Applicant: Smith & Nephew, Inc., Memphis, TN (US)

(72) Inventors: Rafal Z. Jezierski, Middleton, MA (US); Brian Joseph Loreth, Braintree, MA (US); Camal Shener-Irmakoglu, Woburn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 410 days.

(21) Appl. No.: 14/992,188

(22) Filed: Jan. 11, 2016

(65) Prior Publication Data
US 2016/0113670 A1 Apr. 28, 2016

Related U.S. Application Data

(63) Continuation of application No. 13/472,895, filed on May 16, 2012, now Pat. No. 9,232,958.

(51) Int. Cl.
A61B 17/32 (2006.01)
A61B 90/00 (2016.01)
A61B 17/00 (2006.01)

(52) U.S. Cl.
CPC ........ A61B 17/32002 (2013.01); A61B 90/08 (2016.02); A61B 2017/0023 (2013.01);
(Continued)

(58) Field of Classification Search
CPC ............ A61B 17/32; A61B 17/320016; A61B 17/32002; A61B 17/3205; A61B 17/32053; A61B 17/3207; A61B 17/320758; A61B 17/3209; A61B 17/34; A61B 17/3403; A61B 17/3415; A61B 17/3417; A61B 17/3421; A61B 17/3423; A61B 2017/320024; A61B 2017/320028; A61B 2017/320032; A61B 2017/32004; A61B 2017/320044; A61B 2017/320052; A61B 2017/320056; A61B 2017/320064; A61B 2017/3405; A61B 2017/3433; A61B 2017/3443; A61B 2017/3445;
(Continued)

(56) References Cited

U.S. PATENT DOCUMENTS 3,486,229 A 12/1969 Fischl
4,314,560 A 2/1982 Helfgott et al.
(Continued)

FOREIGN PATENT DOCUMENTS

CN 102131472 7/2011
EP 0623317 A1 9/1994
(Continued)

OTHER PUBLICATIONS

Second Office Action in Japanese Patent Application No. 2015-512684; dated Nov. 13, 2017; 5 pages.
(Continued)

Primary Examiner — Christopher L Templeton
Assistant Examiner — Chima U Igboko

(57) ABSTRACT

A surgical instrument including a reusable and sterilizable hub assembly and a releasably connectable disposable blade assembly allows multiple reuse of the hub assembly in conjunction with single use disposable blade assemblies.

19 Claims, 16 Drawing Sheets

(52) U.S. Cl.
CPC .............. *A61B 2017/00477* (2013.01); *A61B 2090/0813* (2016.02)

(58) Field of Classification Search
CPC .... A61B 2017/3447; A61B 2017/3449; A61B 2017/22074; A61B 2017/00477; A61B 2017/0046; A61B 2017/0023; A61B 10/02; A61B 10/0233; A61B 10/0275; A61B 2010/0225; A61B 2010/0208; A61B 2090/0813; A61B 90/08; A61B 17/320036; A61B 17/320068; A61B 17/320092; A61B 17/32075; A61B 17/320783; A61B 17/32093; A61B 17/322; A61B 17/326; A61B 17/32056; A61B 17/320708; A61B 17/320725; A61B 2017/320004; A61B 2017/320008; A61B 2017/320012; A61B 2017/320048; A61B 2017/32006; A61B 2017/320069; A61B 2017/32007; A61B 2017/320071; A61B 2017/320072; A61B 2017/320073; A61B 2017/320074; A61B 2017/320078; A61B 2017/32008; A61B 2017/320082; A61B 2017/320093; A61B 2017/320095; A61B 2017/320733; A61B 2017/320741; A61B 2017/320766; A61B 2017/320775; A61B 2017/320791; A61B 2017/32096; A61B 2017/3225; A61B 2017/320716
See application file for complete search history.

(56) References Cited

U.S. PATENT DOCUMENTS

| | | | |
|---|---|---|---|
| 4,577,629 A | | 3/1986 | Martinez |
| 4,662,869 A | | 5/1987 | Wright |
| 4,674,500 A | | 6/1987 | DeSatnick |
| 4,989,583 A | | 2/1991 | Hood |
| 5,019,035 A | | 5/1991 | Missirlian et al. |
| 5,112,299 A | | 5/1992 | Pascaloff |
| 5,217,479 A | | 6/1993 | Shuler |
| 5,231,169 A | | 7/1993 | Constantz et al. |
| 5,376,078 A | | 12/1994 | Dinger, III et al. |
| 5,632,759 A | | 5/1997 | Rexroth |
| 5,766,190 A | * | 6/1998 | Wulfman .......... A61B 17/1617 606/159 |
| 5,766,200 A | | 6/1998 | Mazurek et al. |
| 5,800,398 A | * | 9/1998 | Hahnle ............ A61B 17/3417 604/164.11 |
| 5,807,338 A | | 9/1998 | Smith et al. |
| 5,921,956 A | * | 7/1999 | Grinberg .............. A61B 1/0052 600/146 |
| 6,007,554 A | | 12/1999 | Van Ess |
| 6,494,892 B1 | | 12/2002 | Ireland et al. |
| 6,695,782 B2 | * | 2/2004 | Ranucci .......... A61B 17/22012 600/439 |
| 7,666,200 B2 | | 2/2010 | Heisler |
| 8,142,388 B2 | | 3/2012 | Gomez |
| 2002/0055754 A1 | | 5/2002 | Ranucci et al. |
| 2003/0093103 A1 | * | 5/2003 | Malackowski .... A61B 17/1626 606/170 |
| 2003/0163134 A1 | | 8/2003 | Riedel et al. |
| 2003/0233111 A1 | * | 12/2003 | Patel ................ A61B 17/32002 606/170 |
| 2004/0111060 A1 | | 6/2004 | Racenet et al. |
| 2004/0122460 A1 | | 6/2004 | Shores et al. |
| 2006/0025792 A1 | | 2/2006 | Gibson et al. |
| 2006/0217751 A1 | * | 9/2006 | O'Quinn .......... A61B 17/32002 606/180 |
| 2007/0196764 A1 | | 8/2007 | Hirosaki et al. |
| 2007/0260275 A1 | | 11/2007 | Ahlberg et al. |
| 2008/0140013 A1 | | 6/2008 | Kunkel et al. |
| 2009/0048485 A1 | | 2/2009 | Heisler |
| 2009/0326531 A1 | | 12/2009 | Geiselhart |
| 2010/0249786 A1 | | 9/2010 | Schmieding et al. |
| 2010/0262166 A1 | | 10/2010 | Boraiah et al. |
| 2010/0286616 A1 | | 11/2010 | Baroud |
| 2011/0004163 A1 | | 1/2011 | Vaidya |
| 2012/0109130 A1 | | 5/2012 | Casey et al. |
| 2013/0060272 A1 | * | 3/2013 | Thistle ............ A61B 17/32002 606/170 |

FOREIGN PATENT DOCUMENTS

| | | |
|---|---|---|
| WO | 199743958 | 11/1997 |
| WO | 199836695 | 8/1998 |
| WO | 2009023607 | 2/2009 |
| WO | 2010135812 | 12/2010 |

OTHER PUBLICATIONS

Third Office Action in Chinese Patent Application No. 201380037990.X; dated Oct. 20, 2017; 5 pages.
Second Office Action in Chinese Patent Application No. 201380037990.X; dated Apr. 5, 2017; 8 pages.
Office Action for Chinese Patent Application No. 201380037990.x, dated Aug. 12, 2016.
Office Action for Australian Patent Application No. 2013263235, dated Nov. 28, 2016.
International Search Report and Written Opinion, dated Jul. 25, 2014, PCT/US2013/039796, 11 pages.

* cited by examiner

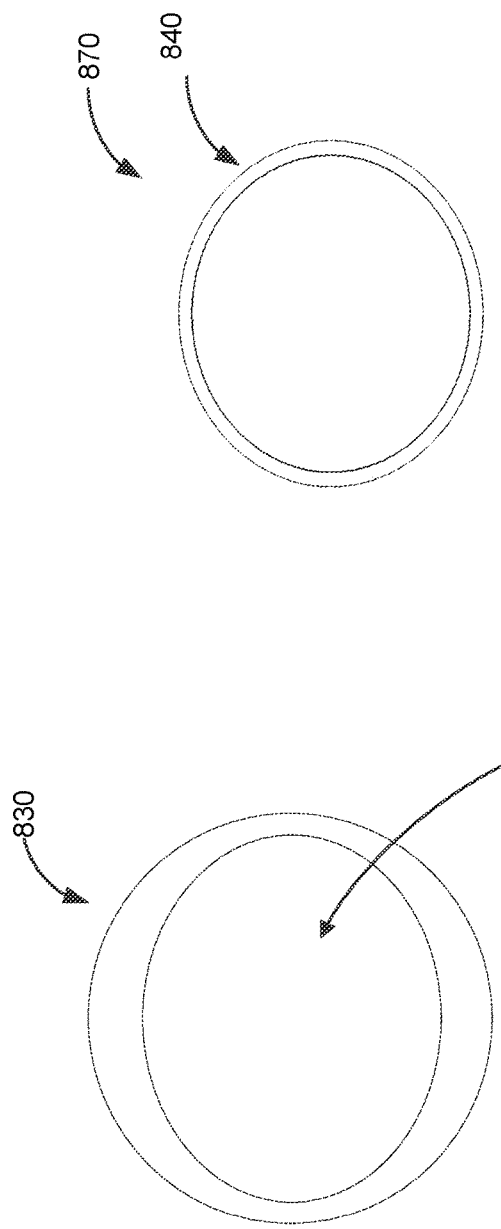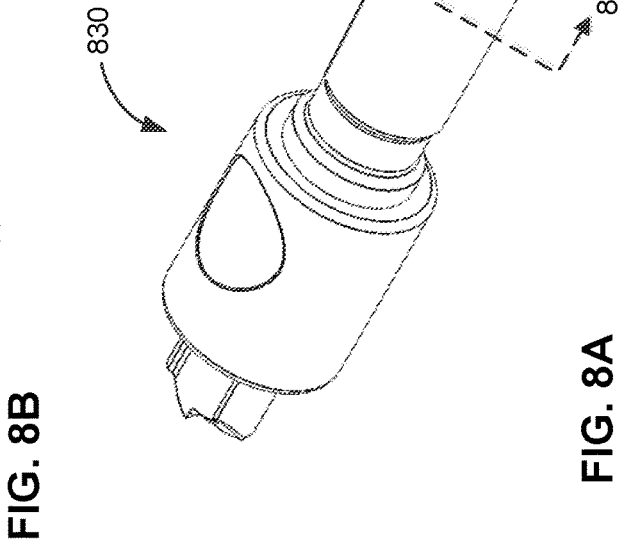

REUSABLE BLADE HUB ASSEMBLY

FIELD OF INVENTION

The present disclosure relates generally to surgical instruments and, more specifically, to a rotary surgical instrument for cutting tissue.

BACKGROUND

Powered arthroscopic surgical instruments typically include a rigid, stationary outer tube within which a rigid inner tube is rotated by a motor. A cutting implement, such as a blade or abrading burr, is disposed on the distal end of the inner tube. Tissue or bone is exposed to the cutting implement through an opening in the distal end of the outer tube, and tissue or bone fragments cut by the rotating blade or burr are drawn through the interior of the inner tube, along with irrigating fluid, by the use of suction applied at the proximal end of the instrument.

A motorized attachment engages a hub, typically on the inner tube, and rotates the inner tube within the outer tube for providing cutting movement and force. The motorized attachment also incorporates a suction attachment for evacuating cut matter from a surgical extraction site through the hollow tubes. Several surgical instruments of various complementary functions are often employed when performing surgical procedures, one function of which is the controlled cutting and evacuation of tissue and bone fragments.

Conventional single use arthroscopic blades typically use a non-reusable plastic hub assembly permanently integrated with metallic outer tubes and inner tubes containing cutting edges. The hub assembly is disposed of in its entirety at the conclusion of an operating procedure. The conventional hub assembly components including an outer hub and inner hub are typically each formed from a single piece of injection molded plastic.

Conventional multiple use arthroscopic blades include a metallic hub assembly permanently integrated with metallic tubes containing cutting edges. This assembly is reprocessed at the conclusion of each use and the cutting edges are periodically reconditioned.

SUMMARY

Conventional approaches to reuse of arthroscopic surgical instruments suffer from shortcomings in cost and reusability because conventional surgical instruments employ blades and tubes that are permanently affixed to a corresponding inner hub and outer hub, respectively. Therefore, the entire blade, tube, hub assembly must be disposed or somehow effectively sterilized. Configurations disclosed herein are based, in part, on the observation that a disposable blade assembly can be designed to be releasably engaged to a reusable hub assembly. The hub assembly is also designed to be sturdier and more easily sterilized. It would be beneficial, therefore, to provide a reusable and sterilizable hub assembly, and a disposable blade assembly, releasably connectable to the hub assembly to avoid the need to dispose of hub components. Such an assembly would also avoid any problems associated with trying to sterilize tubes and blades while they are affixed to hubs and drive shafts.

Accordingly, configurations herein substantially overcome the shortcomings of conventional surgical instruments by combining a reusable hub assembly having an outer hub and an inner hub insertable into the outer hub with a disposable blade assembly releasably connectable to the hub assembly. The disposable blade assembly has an outer tube releasably connectable to the outer hub, and an inner tube releasably connectable to the inner hub. Such an instrument reduces the disposable assembly to a disposable blade assembly including metallic cutting members (e.g., outer tube edgeform and inner tube edgeform). The disposable blade assembly which no longer includes the inner and outer hub provides a lower unit cost and eliminates problems associated with attempts to sterilize the blade assemblies especially when the blades are permanently fixed to hubs or drive shafts. Other savings include reduced packaging cost, reduction in sterilization costs, lower disposal costs, reduced environmental impact due to elimination of disposable plastic components, and diminished environmental impact due to reduction in packaging volume. In one embodiment, the reusable blade hub assembly can be attached to existing motor drive units (MDUs) and existing controls, thus avoiding the need to acquire a new MDU, controls or any surgical technique modification.

In further detail, the disclosed reusable and sterilizable hub assembly includes an outer hub having an inner hub cavity, an outer tube receiving channel for releasably receiving a disposable outer tube and an outer tube retainer. The hub assembly further includes an inner hub insertable into the inner hub cavity of the outer hub comprising an inner channel for receiving a disposable inner tube, the inner channel having an opening for releasably engaging the disposable inner tube.

By reusing the hub assembly, optional coding magnets which interact with Hall-effect devices to identify the type of surgical instrument can be reused, because in the disclosed configurations the magnets are embedded in the reusable hub assembly. Such an assembly allows attachment and removal of disposable metallic cutting members. The attachment and locating mechanisms are integrated into the hub assembly along with corresponding features incorporated into the inner and outer tubes.

In order to operate correctly, the disposable outer tube is fixed both rotatably and axially with respect to the reusable outer hub. Likewise the disposable inner tube is fixed both rotatably and axially at a proximal end with respect to the reusable inner hub. In order to be disposable, the outer tube is easily releasable from the outer hub and the inner tube is easily releasable from the inner hub. In other words, after the disposable blade assembly is inserted into the hub assembly, the outer tube will not substantially rotate with respect to the outer hub or slip into or out of the outer hub, and the inner tube rotates in conjunction with the inner hub without slipping. Many of the features which allow releasability and provide rotational and axial retention are predominantly associated with the reusable hub assembly to minimize costs associated with the disposable components. Some of these features are described below.

A disposable blade assembly for use with a reusable hub assembly comprising an inner hub and an outer hub, the disposable blade assembly includes an elongate outer tube having a distal region with an opening, and an outer cross section for releasable engagement with an outer hub. The blade assembly further includes an elongate inner tube rotatably disposed at least partially within the elongate outer tube, having a proximal end cross section with a profile for releasable engagement with a corresponding inner hub inner channel, and a distal region comprising a cutting member. The cutting member is adjacent to the outer tube opening and permits resection of bodily tissue. The disposable blade assembly allows for rapid assembly of the blade components (i.e., inner and outer tubes) together with the hub assembly in an operating room environment, without utilization of tools or additional hardware. Upon completion of the surgical procedure, the surgical instrument can be disassembled to allow the hub assembly to undergo a reprocessing cycle, while the single use cutting blades are disposed.

In an example arrangement, the outer hub geometry provides full compatibility with existing handpieces (MDUs) by including an MDU latching member incorporated into the hub assembly. In this arrangement, the hub assembly has a metal construction and is autoclavable. The outer tube has an asymmetrical outer cross section matching the outer hub receiving channel cross section, to orientate an edgeform opening in relation to the MDU, and to prevent radial dislocation of the tube. The hub assembly includes a retainer. The retainer includes a separate retaining cap joined via threaded attachment to a fixed retaining member disposed at a distal region of the outer hub. In other arrangements, inner tubes have differing non-circular cross sections. In a particular arrangement, the inner tube has an oval cross section extending for a portion of the proximal end of the inner tube while the remaining portion of the tube has a circular cross section. The oval cross section corresponds to an inner hub inner channel cross section for effective torque transfer between the inner hub and the inner tube.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention. In the drawings:

FIG. 8A shows a perspective view of another embodiment of the distal end of an inner hub of the hub assembly of FIG. 2;

FIG. 8B shows a cross section view of FIG. 8A taken along lines 8B-8B of FIG. 8A;

FIG. 8C shows a cross section view of the outer non-circular cross section of the inner tube for releasable engagement with the inner hub outer tube of FIG. 8A;

DETAILED DESCRIPTION

A surgical instrument including a reusable and sterilizable hub assembly and a releasably connectable disposable blade assembly allows multiple reuse of the hub assembly in conjunction with a single use disposable blade assembly. Depicted below are example configurations of the surgical instrument as disclosed and claimed herein. The disposable blade assembly includes a disposable outer tube and disposable inner tube. The disposable outer tube is fixed both rotatably and axially with respect to the reusable outer hub. Likewise a disposable inner tube is fixed both rotatably and axially at a proximal end with respect to the reusable inner hub. In order to be disposable, the outer tube is easily releasable from the outer hub and the inner tube is easily releasable from the inner hub.

Figure 1A:
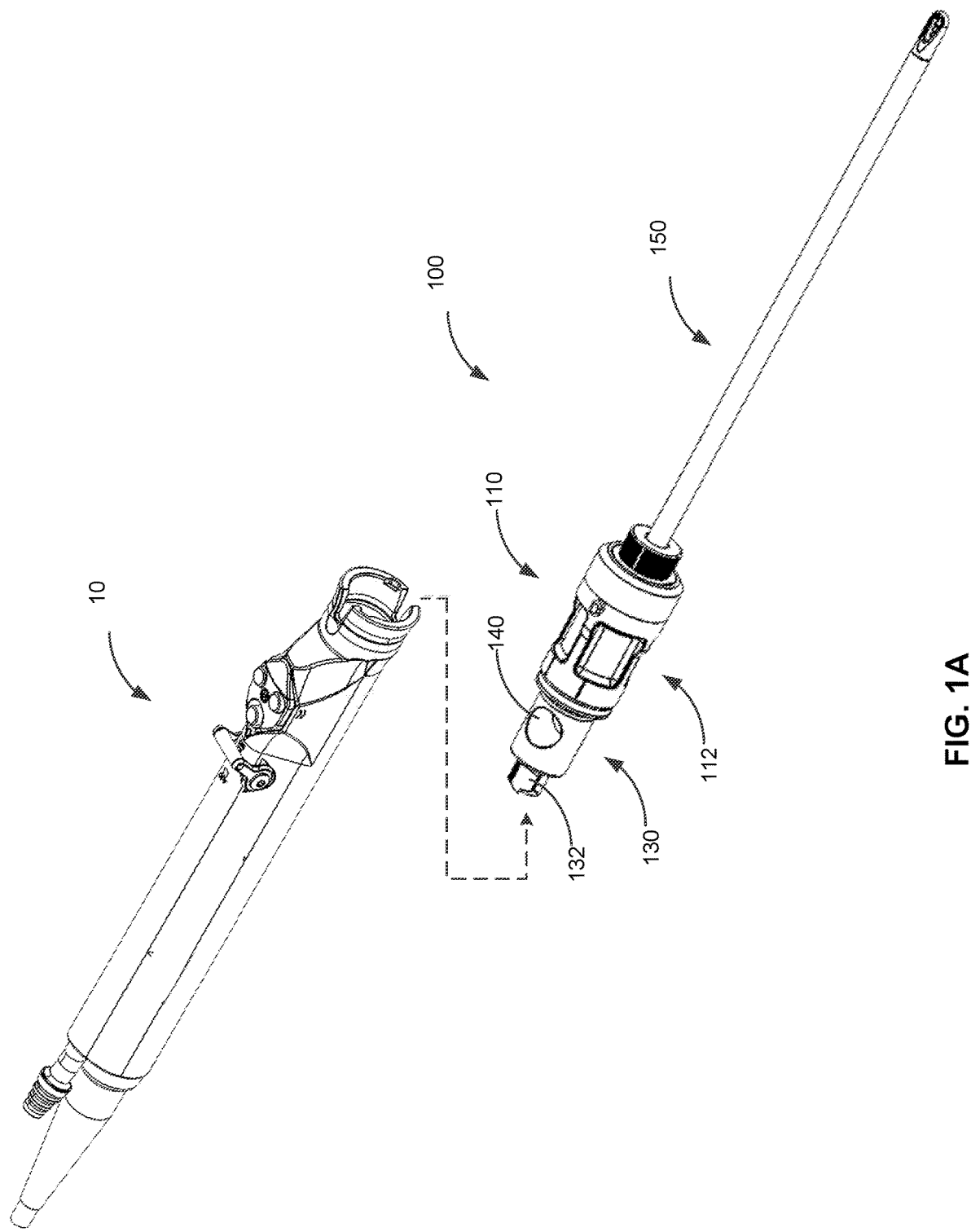
FIG. 1A is a perspective view of an assembled surgical instrument as disclosed herein.

FIG. 1A is a view of a surgical instrument 100 as disclosed herein, including a reusable and sterilizable hub assembly 110 and a disposable blade assembly 150 releasably connectable to the hub assembly 110. The hub assembly 110 includes an outer hub 112 and an inner hub 130 which is insertable into the outer hub 112. In operation, a motor drive unit (MDU) 10 connects to an extension 132 on the inner hub 130. Details of a similar MDU 10 are described in U.S. Pat. No. 5,133,729, which is entitled "Motor-Driven Hand-Piece for a Surgical Tool," U.S. Pat. No. 6,090,122, which is entitled "Surgical Instrument Handpiece and System," and both are incorporated by reference.

Figure 1B:
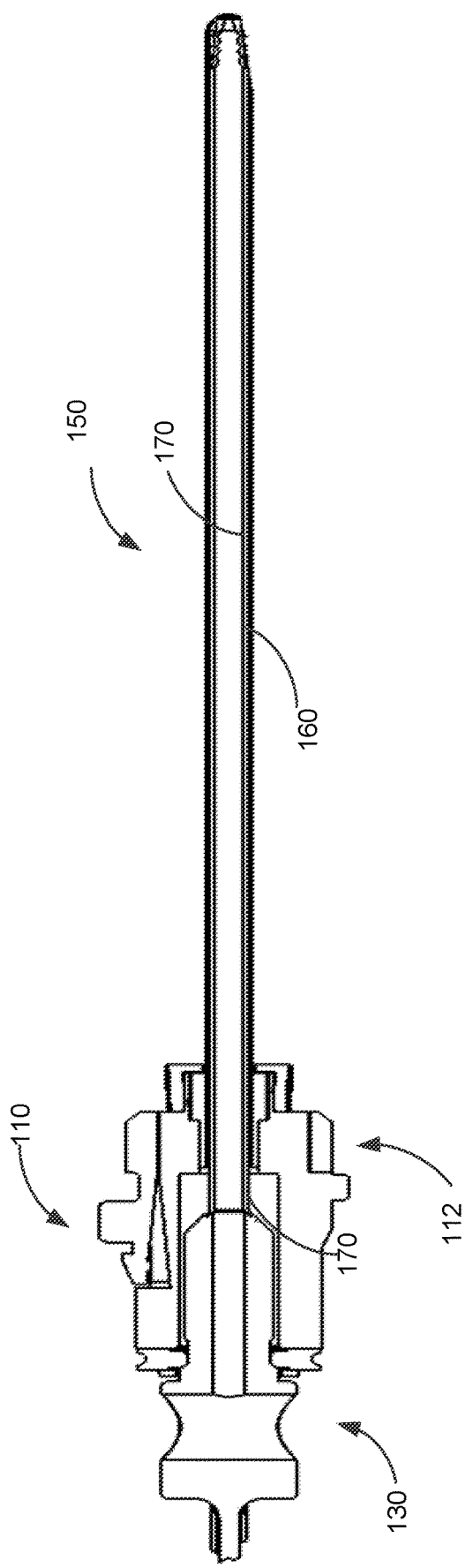
FIG. 1B is a cross sectional side view of the surgical instrument of FIG. 1A.

FIG. 1B is a cross sectional side view of FIG. 1A showing additional details of surgical instrument 100. The disposable blade assembly 150 includes an outer tube 160 and an inner tube 170 rotatably disposed at least partially within the outer tube 160. In one embodiment, the disposable blade assembly 150, or separately the inner tube 170 or the outer tube 160, can be quickly released from the hub assembly 110 without requiring any special tools. This is useful, for example, to change blades during an operation.

Figure 1C:
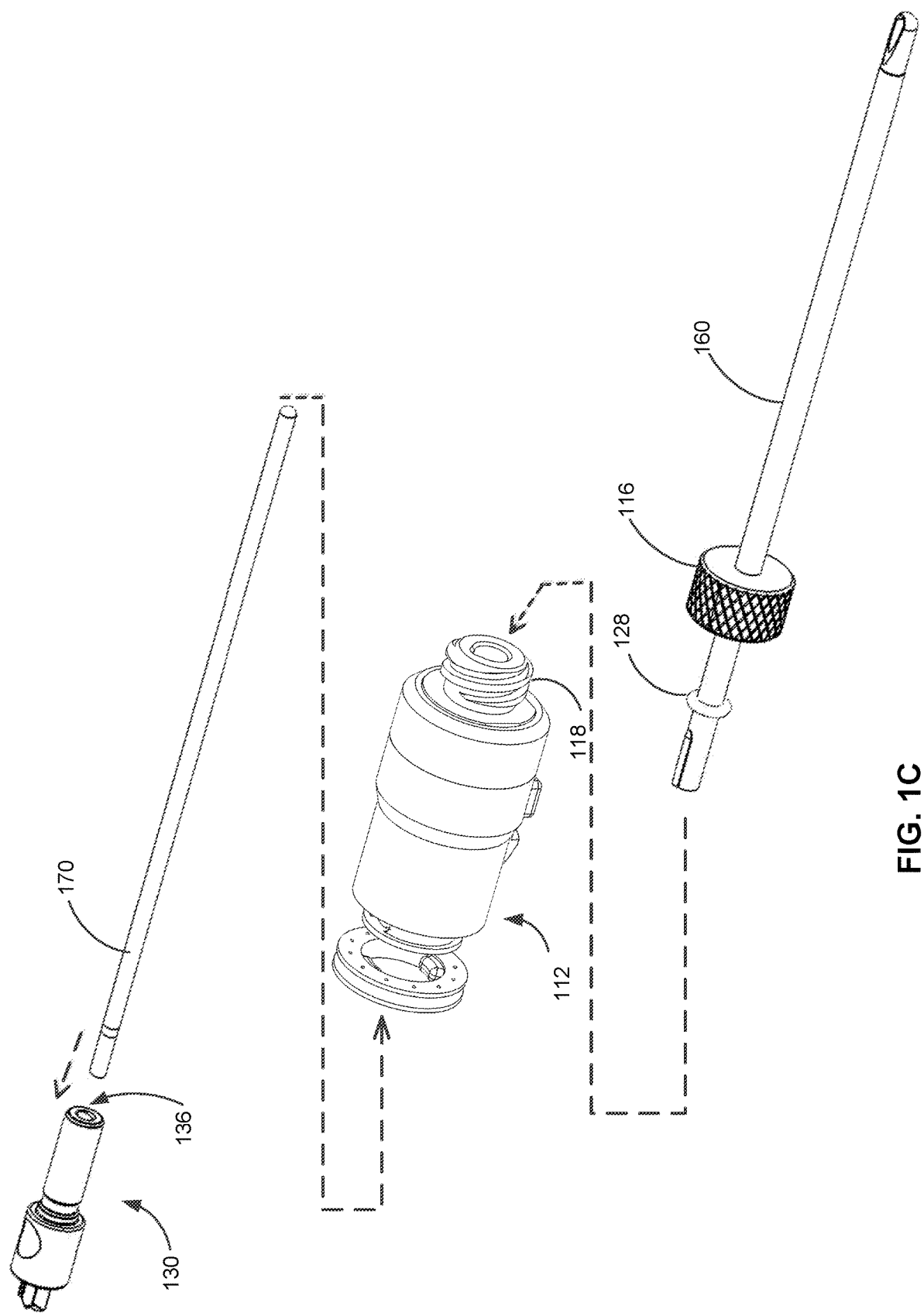
FIG. 1C is an exploded view of the surgical instrument of FIG. 1A.
Figure 2:
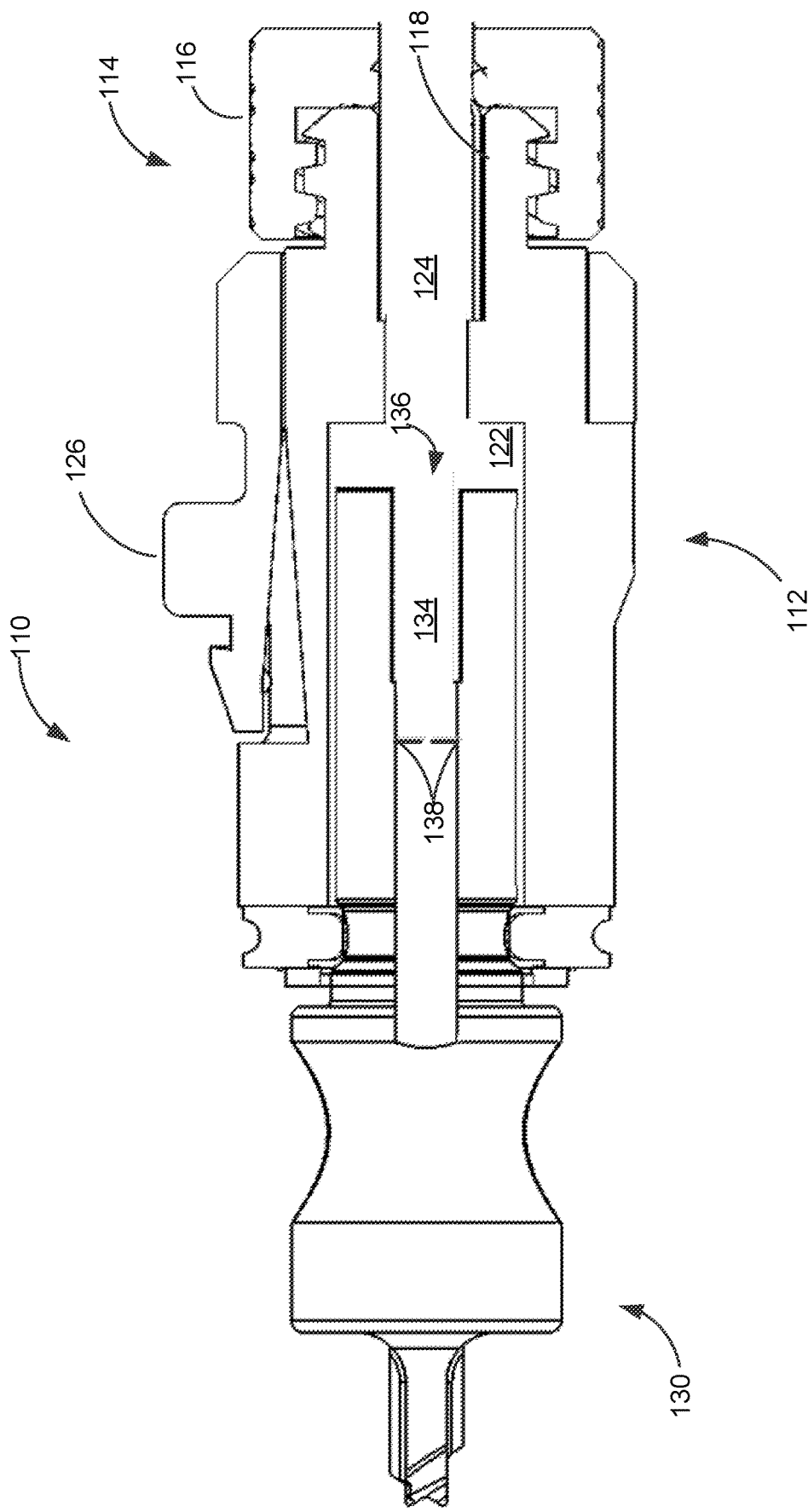
FIG. 2 shows a cross section view of a hub assembly of the surgical instrument of FIG. 1A, including an outer tube retainer.

Now referring to FIGS. 1C and 2, there are several ways to assemble the surgical instrument 100 two of which described below:

A first method shown in FIG. 1C for assembling the surgical instrument 100 having a reusable hub assembly 110 and a disposable blade assembly 150 includes:

aligning a proximal end cross section of an inner tube 170 with an inner hub inner channel opening 136;

inserting the inner tube proximal end into the inner channel until fully seated against a bottom of an inner hub stop 138 (FIG. 2);

aligning a proximal end cross section of an outer tube 160 with an outer hub receiving channel opening 124 (FIG. 2);

inserting the proximal end of the outer tube 160 into the outer hub receiving channel 124 until seated against a bottom of the outer hub receiving channel;

engaging an outer tube retainer 114 to retain the outer tube which includes an O-ring 128;

assembling the inner hub 130 into the outer hub 112; and finally latching the surgical instrument 100 onto the motor drive unit 10.

A second method includes:

inserting the proximal end of the blade assembly 150 into the distal end of the hub assembly 110;

manipulating the inner tube proximal end until fully seated against the inner hub stop 138 of the inner channel;

manipulating the outer tube 160 proximal end until seated against the bottom of the outer hub receiving channel 124; and engaging an outer tube retainer 114 to retain the outer tube 160; and finally latching the surgical instrument 100 onto the motor drive unit 10.

Figure 3:
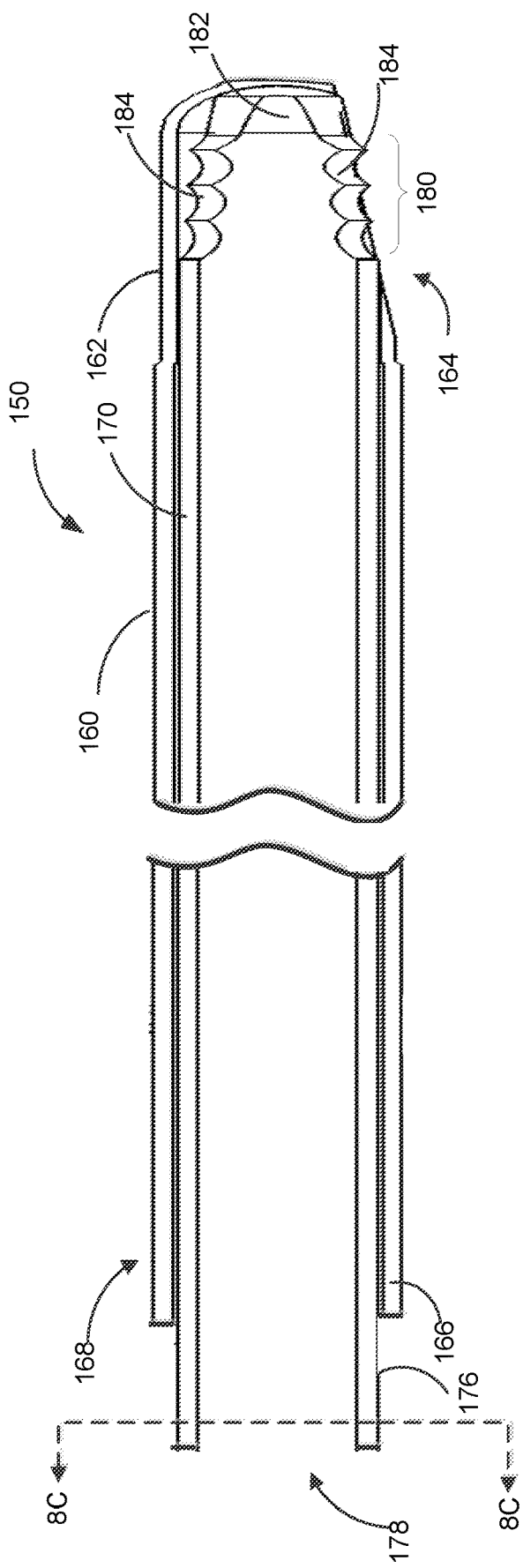
FIG. 3 shows a cross section view of a disposable blade assembly for use with the hub assembly of FIG. 2.

Now referring to FIGS. 2 and 3, the hub assembly 110 includes an outer hub 112 having an inner hub cavity 122, and an outer tube receiving channel 124 for releasably receiving the disposable outer tube 160 of the disposable blade assembly 150. The outer hub 112 includes an outer tube retainer 114 including alignment and retaining features. The hub assembly 110 further includes an inner hub 130 insertable into the inner hub cavity 122 of the outer hub 112. The inner hub includes an inner channel 134 for receiving the disposable inner tube 170 of the disposable blade assembly 150, the inner channel having an opening 136 for releasably engaging the disposable inner tube 170.

In one embodiment, the purpose of the retainer 114 is to releasably, rotatably fix and axially retain the disposable outer tube 160. In another embodiment where the outer tube 160 is partially closed on the distal end, the inner tube 170 is also axially retained. After assembly, the disposable outer tube is prevented from advancing distally by the outer tube retainer 114. During operation the disposable outer tube is prevented from rotating with respect to the outer hub by the outer tube retainer 114 and additional features described below. It will be appreciated that there are many ways to retain the outer tube, including but not limited to a snap fit system, a compressible tapered seal, splined tabs, and a collet chuck. Also shown is a stop member 138 disposed within the inner channel 134 to prevent proximal advancement of the inner tube 170.

In one embodiment, the outer hub 112 is a one piece machined metal component. In this embodiment the inner hub 130 is also one piece machined metal component. While in this embodiment the outer hub 112 and inner hub 130 are made from stainless steel to render the instrument readily sterilizable and reusable, alternatively, the outer hub and the inner hub can be made from other materials including but not limited to non-ferrous metals, polymers, reinforced polymers such as glass filled and carbon fiber.

Referring again to FIG. 3 the disposable blade assembly 150 includes a disposable elongate outer tube 160 having a proximal end 166, a distal region 162 and an opening 164 disposed in the distal region 162 of the outer tube 160. The outer tube 160 has an outer cross section 168 (as shown in cross section in FIG. 7B for one embodiment) for releasable engagement with an outer hub 112. The disposable blade assembly 150 further includes a disposable elongate inner tube 170 rotatably disposed at least partially within the elongate outer tube 160. The inner tube 170 has a proximal end cross section 178 (as shown in cross section in FIG. 8C for one embodiment) having a cross-section for releasable engagement with a corresponding inner hub inner channel 134 (FIG. 2), a distal region 180 at a distal end 182 and a cutting member 184 disposed in the distal region 180 of the inner tube 170. The cutting member 184 is adjacent the outer tube opening 164 to permit resection of bodily tissue. In various embodiments the cutting member can be a blade or a burr. In an embodiment which is compatible with conventional handpieces, the inner hub 130 includes an opening 140 (FIG. 1A) that permits material drawn through inner tube to pass into an aspiration channel (not shown) of the handpiece (not shown).

Figure 5:
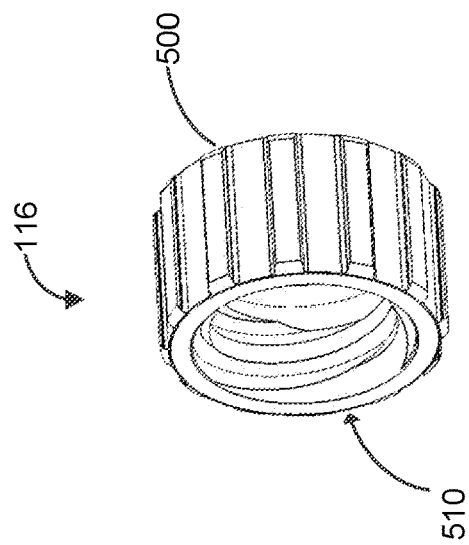
FIG. 5 is a perspective view of a separate outer tube retaining member which engages the fixed member of the outer tube retainer of FIG. 4.
Figure 4:
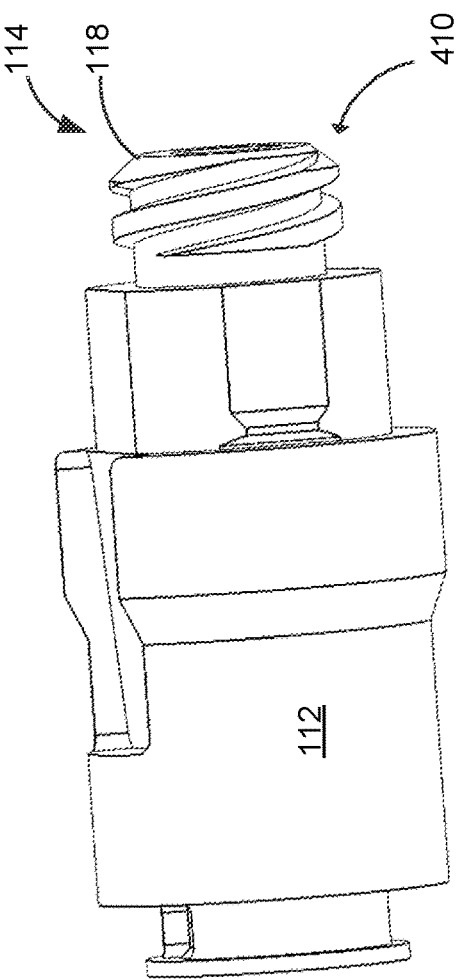
FIG. 4 is a perspective view of the outer hub of FIG. 2 including a fixed member of the outer tube retainer.

Referring to FIGS. 4 and 5, the outer tube retainer 114 includes a fixed member 118 disposed at a distal region of the outer hub 112, and a separate retaining member 116. In one embodiment the outer tube retainer fixed member 118 includes a threaded region 410 and the outer tube separate retaining member 116 is a removable cap 500 having a threaded region 510 to connect to threaded region 410.

Figure 6A:
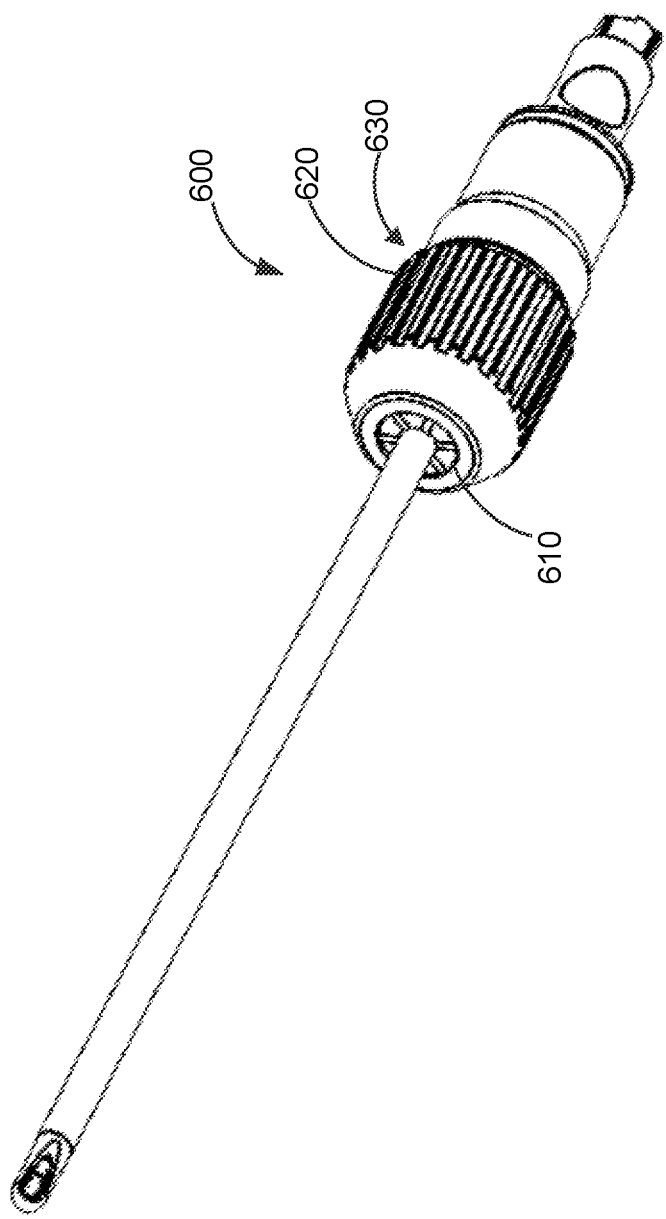
FIG. 6A is a perspective view of a collet chuck embodiment of the separate outer tube retaining member.
Figure 6C:
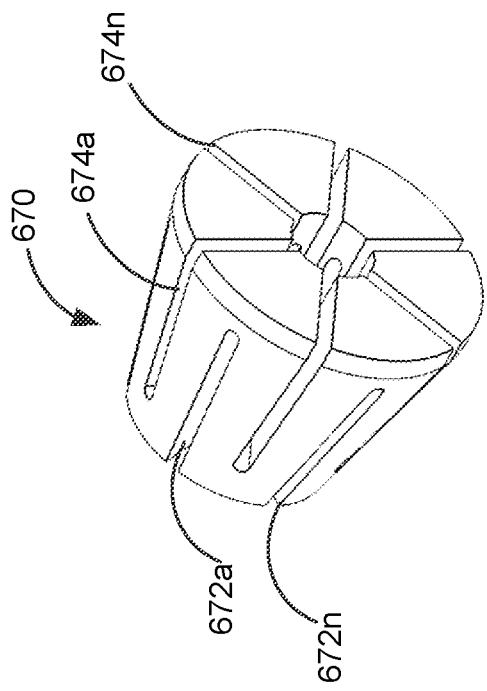
FIG. 6C is a perspective view of an alternate collet used with collet chuck embodiment of FIG. 6A.
Figure 6B:
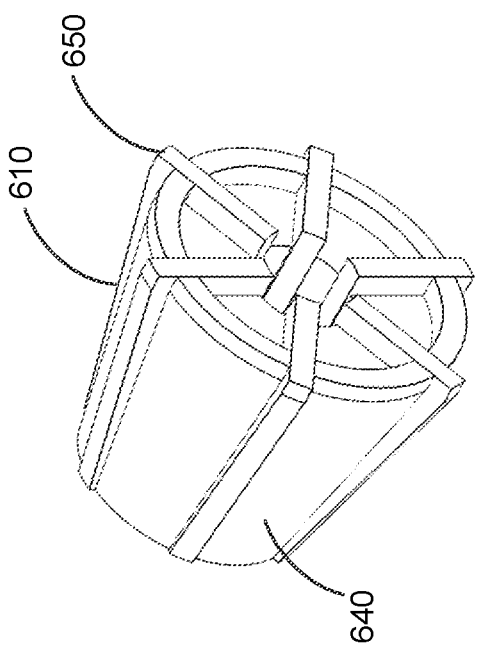
FIG. 6B is a perspective view of a flexible collet of the collet chuck embodiment of FIG. 6A.
Figure 6D:
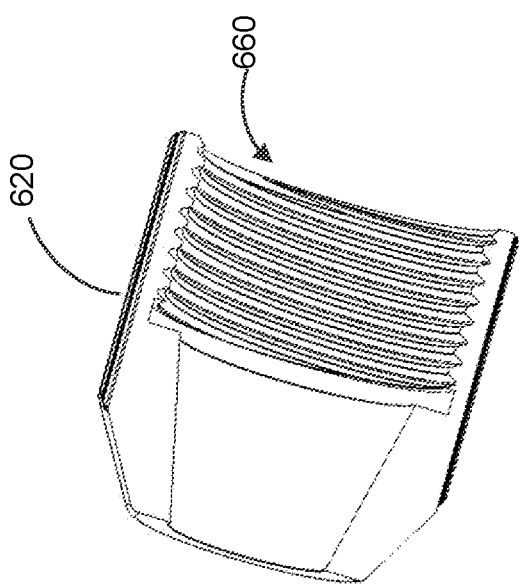
FIG. 6D is a section view of a nose cap of the collet chuck embodiment of FIG. 6A.

The outer tube 160 and the outer hub 112 are secured in rotational and axial communication by any suitable manner, such as threaded regions 410 and 510, respectively, which, after being engaged, serve to prevent the outer tube 160 from sliding back out of the outer hub 112. A snap fit system adapted to mate with a corresponding snap-fit connection on a proximal end of the outer hub, a pin and groove system adapted to mate with a corresponding pin and groove system (FIG. 11) connection on a removable cap or frictional resilient arrangement may be used instead of the thread regions to accomplish the same goal. In one embodiment, the O-ring 128 (FIG. 1C) is installed on the outer tube 160 and is compressed between the cap 500 and the outer hub 112 to provide a seal for the aspiration channel As shown in FIGS. 6A-6D an alternative retaining mechanism includes a collet chuck 600. The collet chuck 600 includes a collet 610 and a nose cap 620. The collet chuck 600 engages an outer tube retainer fixed member 630 similar to outer tube retainer fixed member 118. The collet chuck 600 allows releasing of the disposable blade assembly 150 without completely removing the nose cap 620. In one embodiment, the collet 610 (FIG. 6B) is a combination of a flexible portion 640 and a ridged portion 650. Such a retainer can advantageously provide a secure fit for improved retention of the out hub. The flexible portion 640 accommodates various inner tube diameters, thus eliminating the need for a collet for each diameter. The flexible portion 640 also provides sealing for the suction attachment. In other embodiments, the material used in the collet could be any type metal or a polymer embedded into any type of flexible material. The nose cap 620 (FIG. 6D) includes a threaded portion 660 to engage with the outer tube retainer fixed member 118. FIG. 6C shows an alternate collet having open slots 672a-672n and 674a-674n.

Figure 7B:
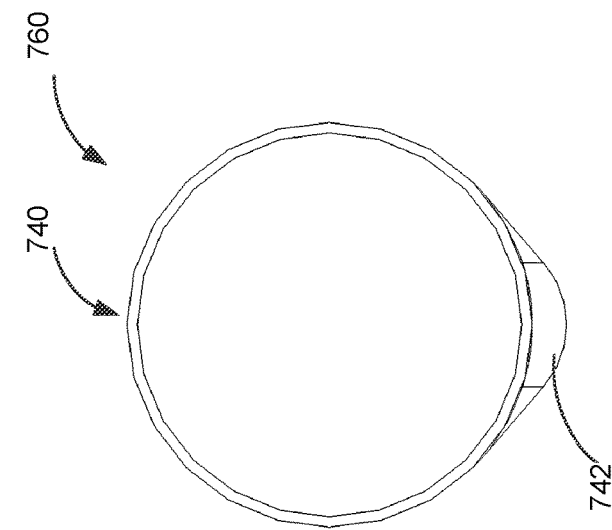
FIG. 7B shows a cross section view of the outer cross section of an outer tube for releasable engagement with the outer hub outer tube of FIG. 7A.
Figure 7A:
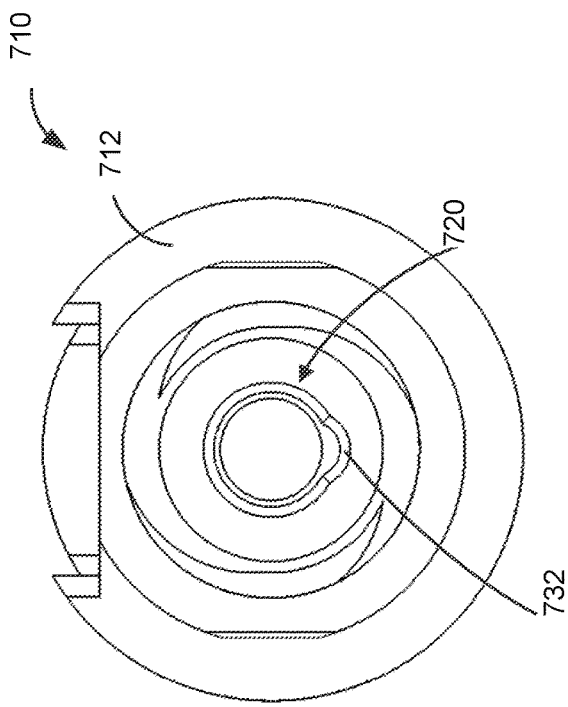
FIG. 7A shows a view of another embodiment of the distal end of the outer hub assembly of FIG. 2.
Figure 7C:
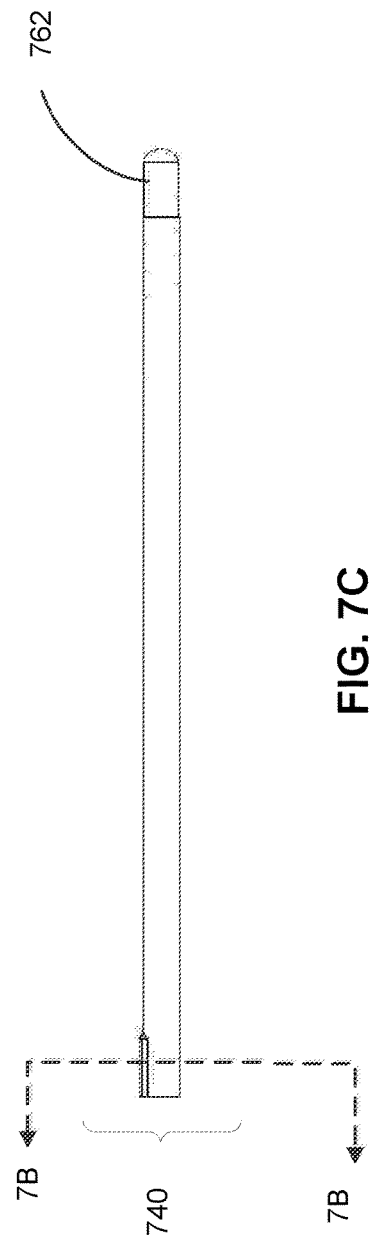
FIG. 7C shows a view along a length of the outer tube of FIG. 7C.

Now referring to FIGS. 7A-7C, a hub assembly 710 includes an outer hub 712 with an outer tube receiving channel cross section 720 which corresponds to an outer cross section 740 of the disposable outer tube 760. In one embodiment, the outer tube receiving channel cross section 720 has an asymmetrical cross section (not shown), and in another embodiment the outer tube receiving channel cross section 720 has a keyed symmetrical cross section with key feature 732, to orient an edgeform opening 762 in the disposable outer tube 760 with respect to a handpiece attached to the hub assembly 710.

FIG. 7B shows the outer cross section 740 of a disposable blade assembly disposable elongate outer tube 760. Here, the outer cross section 740 is a keyed symmetrical cross section with key feature 742 to fit with outer tube receiving channel cross section 720 and to orient the edgeform opening 762 in the disposable outer tube 760 with respect to a handpiece (MDU) attached to the outer hub. As described above, it is also possible to use an asymmetrical outer cross section for the outer tube receiving channel cross section 720.

Orienting the edgeform opening allows a user to grasp the surgical instrument attached to an MDU in a preferred position and have the opening, for example, point straight down or straight up. This feature reproduces the orientation feature of permanently fixed, non-releasable blade and hub conventional devices while maintaining releasability of the disposable blade assembly.

As shown in FIG. 7C, the outer cross section 740 does not need to extend the entire length of the disposable outer tube 760 and can be formed at the proximal end of the outer tube 760 by several methods including, but not limited to, swaging, forming with die set or welding. In one embodiment, length of the profile along the long axis of the disposable outer tube 760 is approximately one cm.

Now referring to FIGS. 8A-8C, an inner hub 830 includes an inner channel opening 820 which corresponds to an outer cross section 840 of a disposable inner tube 870. In one embodiment, the inner channel opening 820 has a non-circular, here an oval cross section and in another embodiment the inner channel opening (not shown) is keyed to match a key on the disposable inner tube (not shown).

FIG. 8C shows the outer cross section 840 of a disposable blade assembly disposable elongate inner tube 870. Here, the outer cross section 840 is non-circular, here an oval, to fit within inner tube channel opening 820.

Figure 9A:
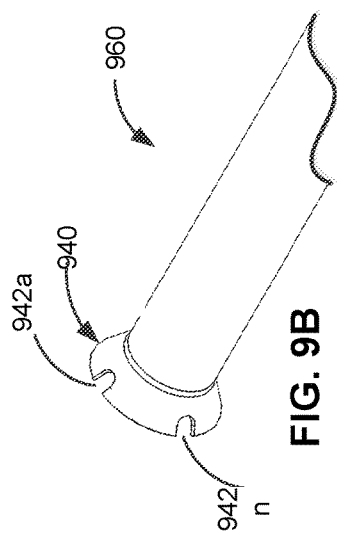
FIG. 9A shows a perspective view of another embodiment of an inner hub of the hub assembly of FIG. 2.
Figure 9B:
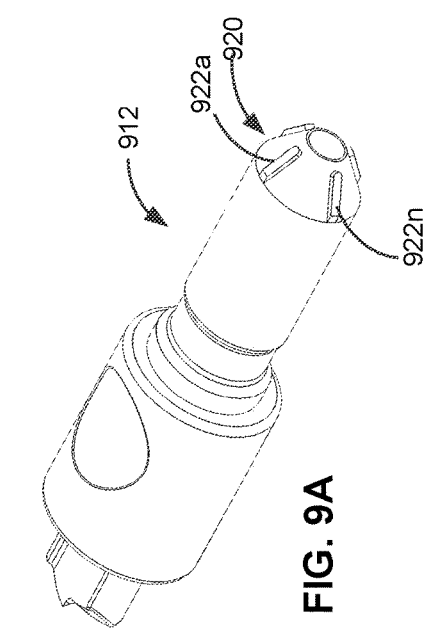
FIG. 9B shows a perspective view of a flanged proximal end of an inner tube for releasable engagement with the inner hub of FIG. 9A.
Figure 9C:
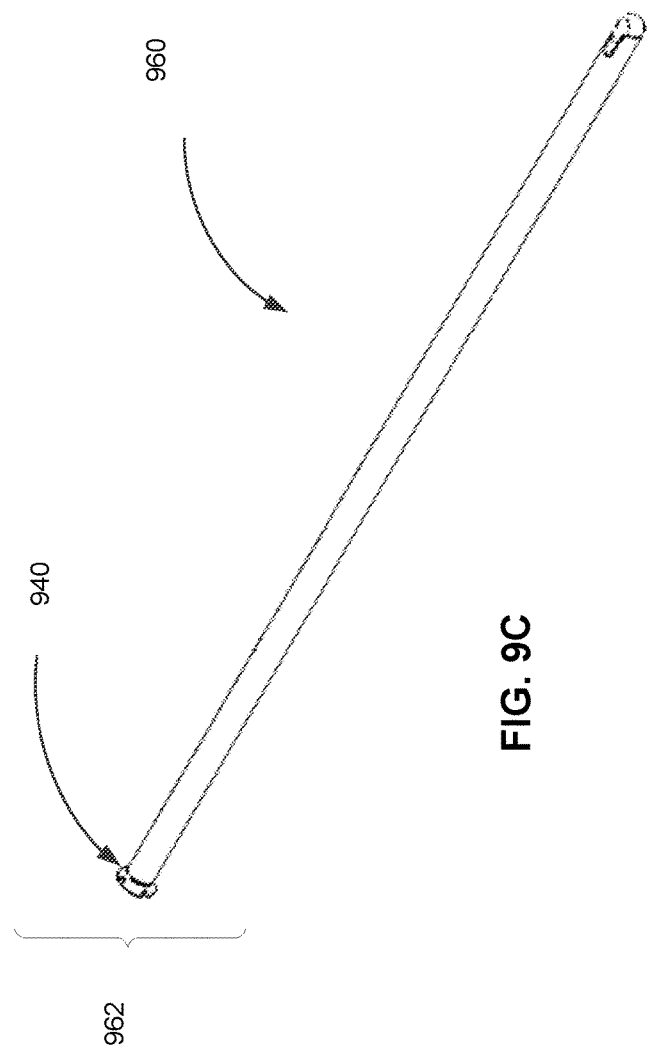
FIG. 9C shows a perspective view of the proximal and distal regions of the inner tube of FIG. 9B.

Now referring to FIGS. 9A-9C, an inner hub 912 has an inner hub surface 920 disposed to receive a flange 940 attached to a proximal end 962 of the disposable inner tube 960. In one embodiment, the flange has alignment grooves 942 a-942 n disposed to engage with corresponding alignment features 922 a-922 n disposed on the surface 920 of the inner hub 912. In one embodiment the alignment features 922 a-922 n are alignment tabs.

The alignment features 922 a-922 n, in conjunction with the inner hub surface 920, provide an inner channel which, when releasably engaged with alignment grooves 942 a-942 n, rotatably fix the disposable inner tube 960 with respect to the inner hub 912. The flange connection provides additional sealing for the aspiration channel.

Figure 10A:
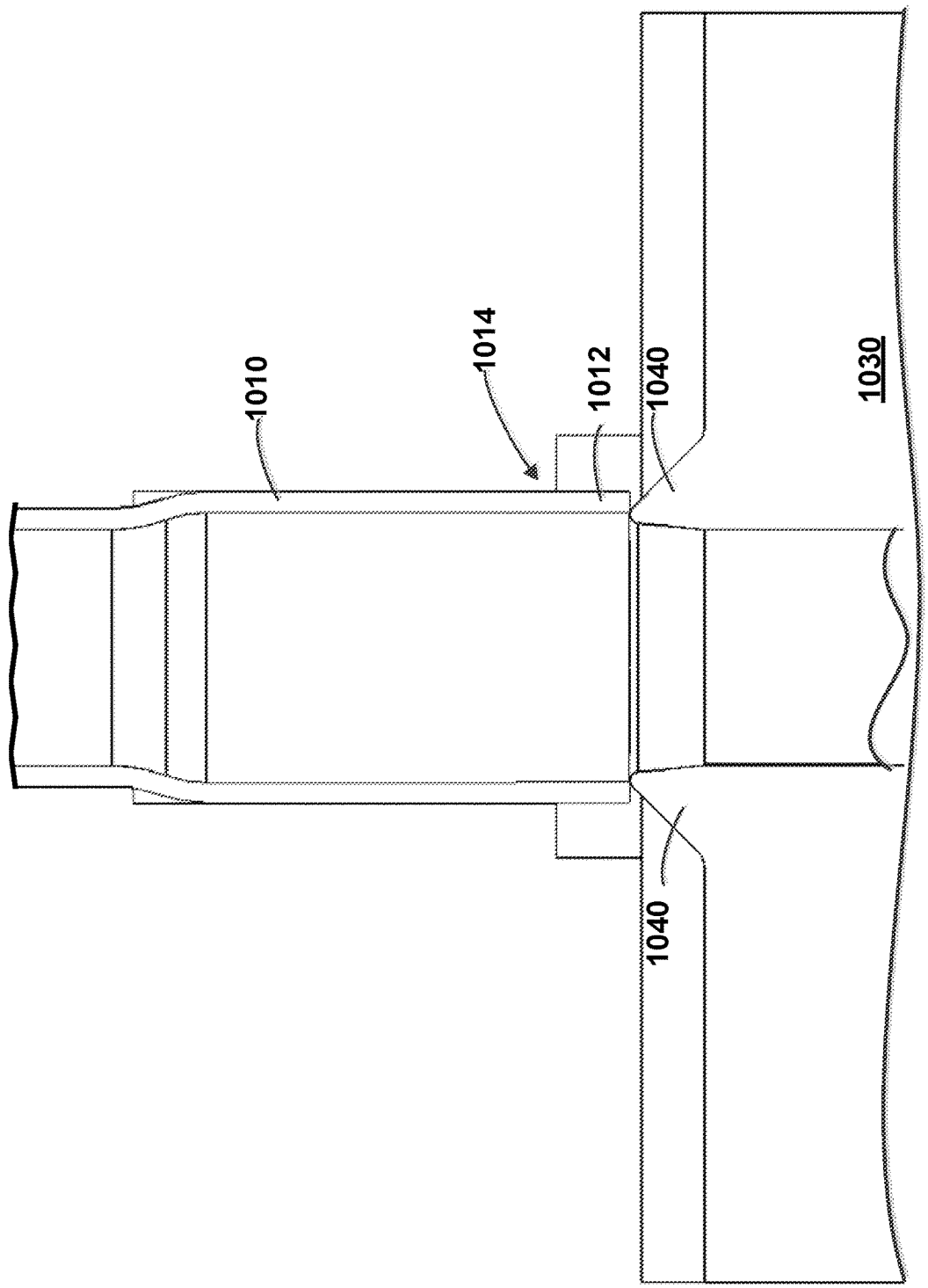
FIGS. 10A and 10B show a cross section view of another embodiment of a swagable outer tube for releasable engagement with the outer hub of the surgical instrument of FIG. 1A.
Figure 10B:
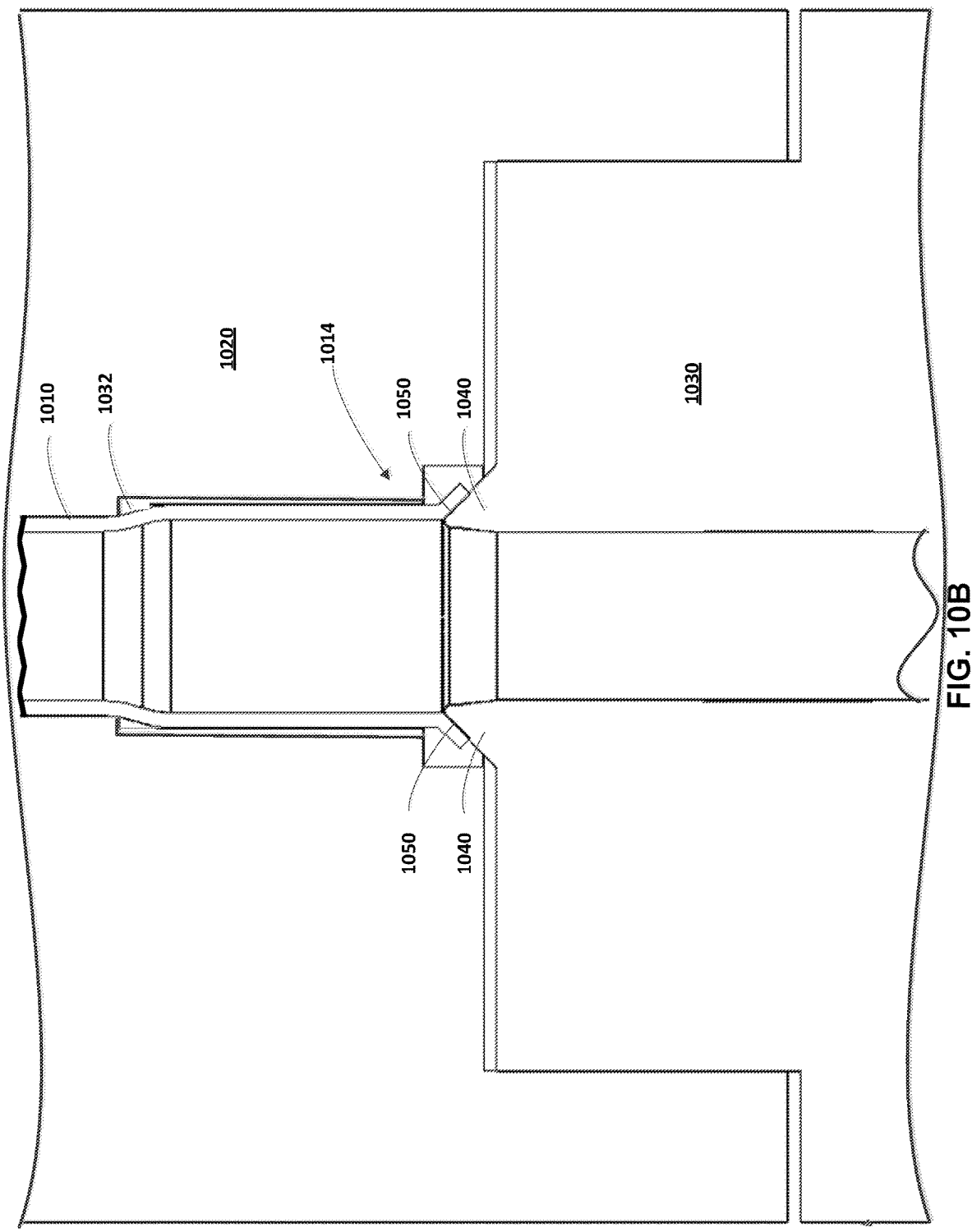

Now referring to FIGS. 10A and 10B, an alternative outer tube 1010 includes a swagable flange section 1012 on a proximal portion 1014 of the outer tube 1010. In one embodiment the outer tube 1010 is a stepped tube. During assembly the outer tube 1010 is inserted into a receiving channel 1032 of an outer cap 1020. An outer tube separate retaining member, here a removable cap, is threaded onto the fixed outer tube retainer (not shown). The threading operation drives the outer tube proximal portion 1014 into outer hub seal bosses 1040. This action causes the seal bosses 1040 to exert axial force on the swagable flange section 1012, thus deforming the swagable flange section 1012 to conform the seal bosses 1040. The result is a seal 1050 between the proximal end of the outer tube and the distal end of the outer hub.

Figure 11:
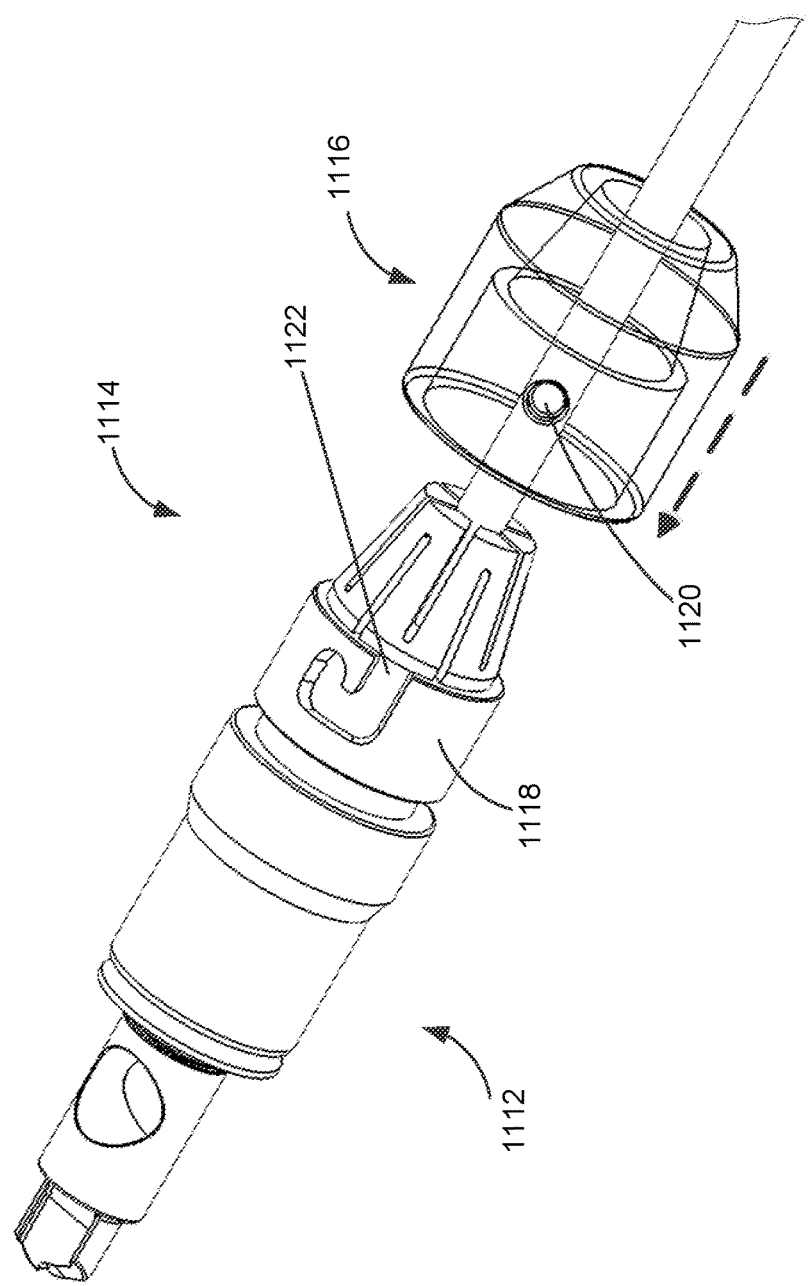
FIG. 11 is a perspective view of a pin and groove embodiment of the separate outer tube retaining member which engages the fixed member of the outer tube retainer similar to the retainer of FIG. 4.
Figure 12:
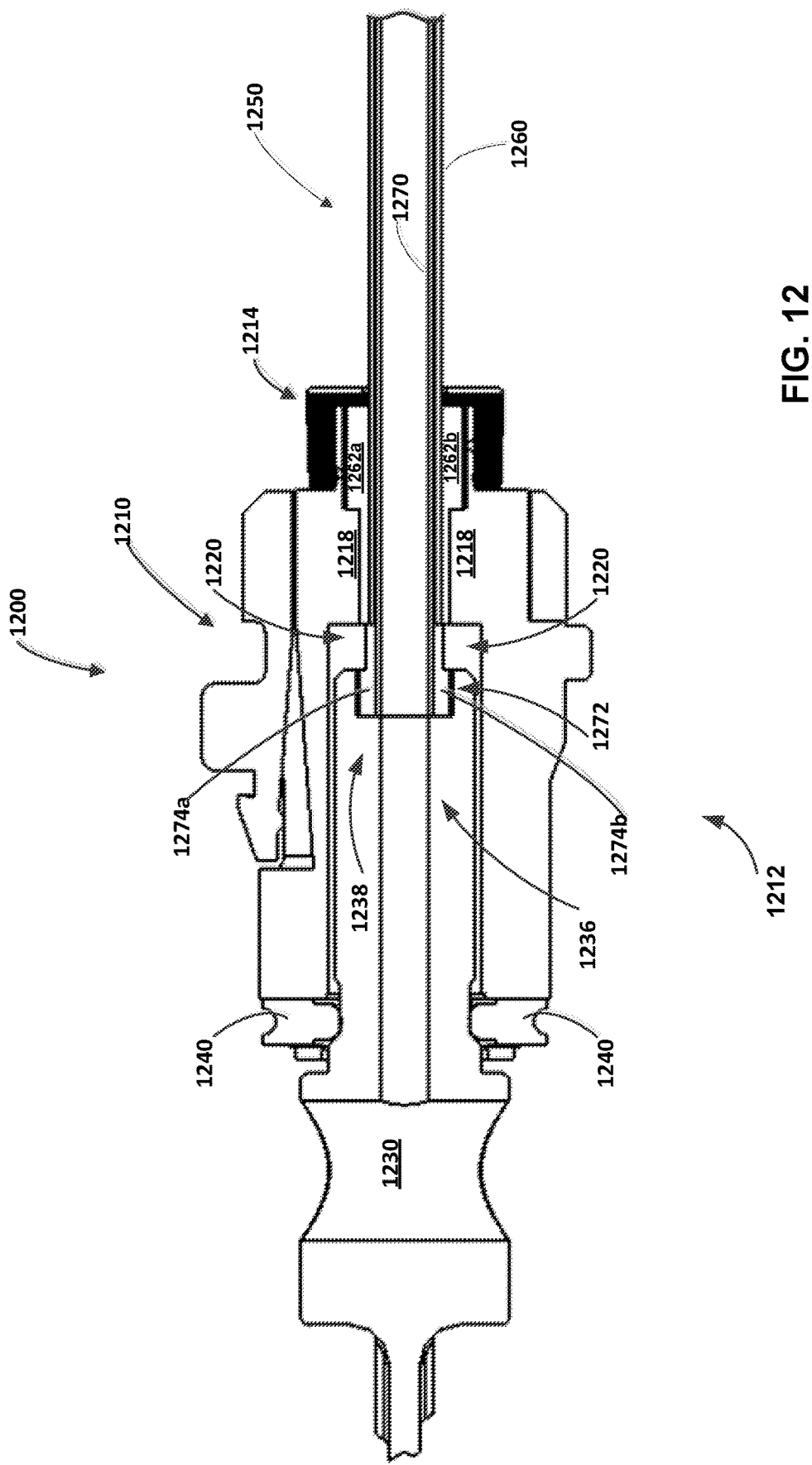
FIG. 12 is a cross section view of another embodiment of the surgical instrument of FIG. 1A having dual locking mechanisms used to secure the disposable blade assembly within the hub assembly.

Now referring to FIG. 11, an alternative outer tube retainer 1114 similar to retainer 114 (FIG. 2) is shown in an open position. The outer tube retainer 1114 includes a fixed member 1118 disposed at a distal region of an outer hub 1112, and a separate retaining member 1116. The outer tube retainer fixed member 1118 includes a "J" shaped groove 1122 and the outer tube separate retaining member 1116 includes at least one pin 1120 to engage with the groove 1122. Here the retainer system is a J-lock and the retaining member 1116 includes two pins 1120 on opposite sides FIG. 12 shows dual locking tabs integrated onto inner and outer tubes. A surgical instrument 1200 similar to surgical instrument 100 includes hub assembly 1210 and a disposable blade assembly 1250. The hub assembly 1210 includes an outer hub 1212 and an inner hub 1230. The hub assembly 1210 includes an outer hub 1212 having an indent 1218 disposed on in inner surface of the outer hub 1212. The disposable blade assembly 1250 includes an outer tube 1260 having tabs 1262a and 1262b (collectively referred as tabs 1262). The indent 1218 receives the tabs 1262 and retains the outer tube 1260 in conjunction with a retainer 1214. The outer tube tabs 1262 are disposed at a proximal end portion of the outer tube 1260 and in conjunction with indents 1218 prevent the outer tube 1260 from being inserted too far into the outer hub 1212 and provide positive feedback of correct engagement. In one embodiment, the tabs 1262 are welded onto the outer tube 1260. The hub assembly 1210 further includes a retainer 1240 which is used for sealing and for retention of the inner hub 1230 during assembly with the disposable blade assembly 1250.

The inner hub 1230 includes an inner channel 1236 having a locking mechanism 1238 for engagement with an inner channel inner tube locking mechanism 1272. In one embodiment, the locking mechanism 1272 includes locking tube members 1274a-1274b which are tabs welded on the inner tube 1270 and the locking mechanism 1238 is a slot in the inner channel 1236. The locking tube members 1274a-1274b abut against a tab 1220 disposed within an inner hub cavity of the outer hub 1212 to prevent the inner tube 1270 from moving axially with respect to the instrument 1200. In another embodiment the inner tube locking members comprise a sleeve having dual tabs arranged on opposite sides of the sleeve, and the sleeve is welded onto the inner tube. This arrangement is useful when the inner tube comprises a burr and an outer tube partially enclosing the inner tube is open at a distal end.

Figure 13:
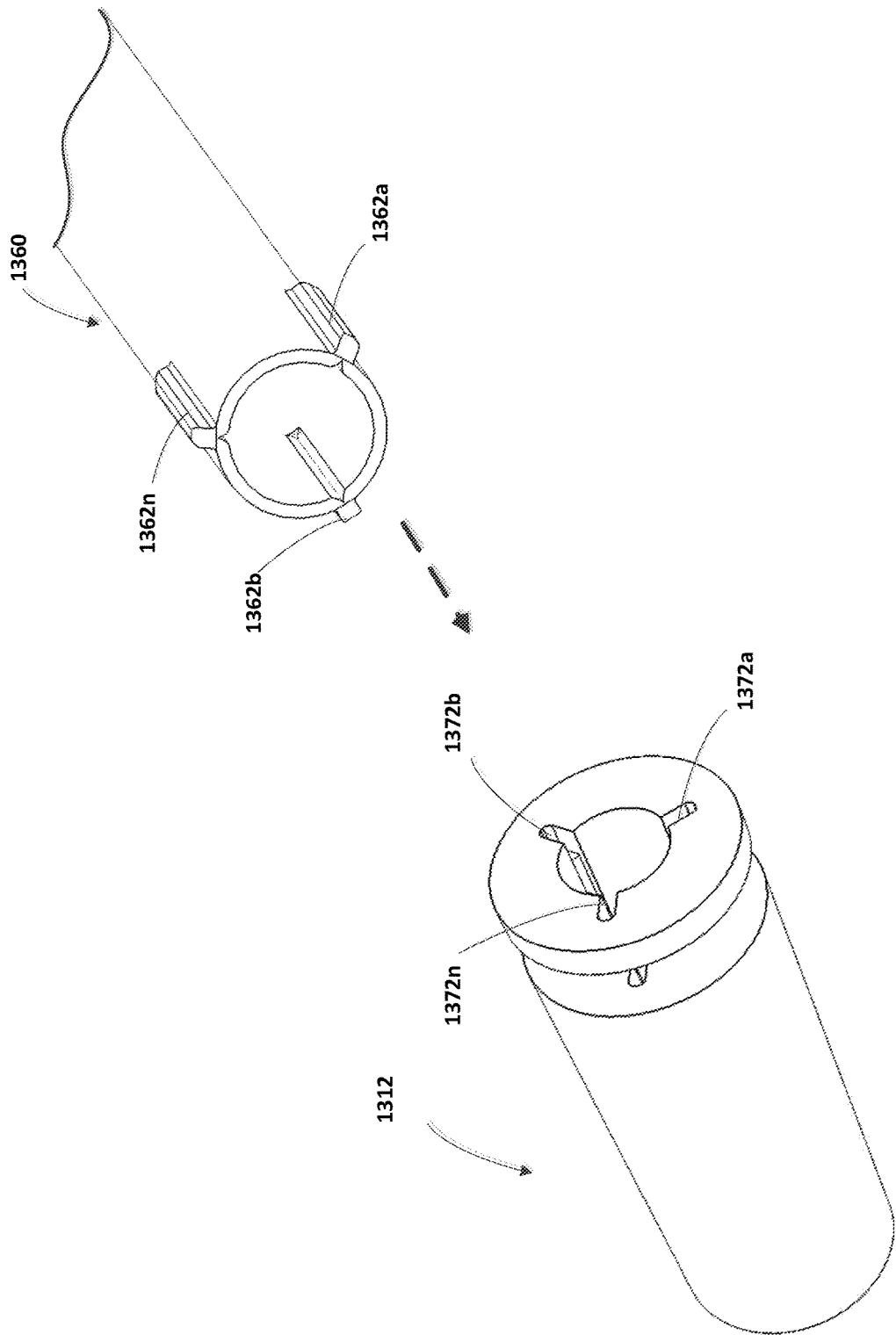
FIG. 13 is a perspective view of a proximal end of a disposable outer tube having alignment tabs which engage an outer hub as disclosed herein.

Now referring to FIG. 13, an alternative disposable outer tube 1360 includes a plurality of alignment tabs 1362a-1362n for engagement with corresponding slots or grooves 1372a-1372n disposed on an inner surface of a proximal portion of an outer hub 1312. The alignment tabs 1362a-1362n serve to rotatably fix the outer tube 1360 with respect to the outer hub 1312 and to align an opening in the outer tube with respect to the outer hub and in turn with respect to a handpiece.

In another embodiment, an inner hub includes internal splines to receive an inner tube having corresponding extruded splines. In yet another embodiment, a disposable blade assembly is secured by the compression of a rubber or silicone seal and a retainer in conjunction with or instead of an O-ring surrounding the outer tube.

Alternative embodiments include other component geometries and features to orient, retain and rotationally fix the disposable blades in the hub assembly. Other features include but are not limited to circular keyed cross sections, detent features as well as symmetrical and asymmetrical designs of the hub channels and the tube cross sections. In alternate arrangements, a snap fit or frictional resilient arrangement may be used instead of the threads and caps to retain the outer tube.

While this invention has been particularly shown and described with references to preferred embodiments thereof, it will be understood by those skilled in the art that various changes in form and details (including hub and tube geometries) may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical instrument comprising:
    a reusable hub assembly comprising:
        an outer hub;
        an inner hub comprising a cylindrical portion defining a cylinder and sharing a longitudinal central axis with the inner hub, the cylindrical portion having a first diameter and terminating along the longitudinal central axis at a distal end, a surface extending from the distal end of the cylindrical portion, the surface defining a conical frustum having a wider width equal to the first diameter and a second diameter less than the first diameter, the surface having a central axis coaxial with the longitudinal central axis, and at least one alignment feature protruding from the surface;
    a disposable blade assembly releasably connectable to the hub assembly comprising: an elongate outer tube releasably connectable to the outer hub; an inner tube releasably connectable to the inner hub; and
        the inner tube comprising a flange extending radially outwardly from the inner tube and defining at least one alignment groove extending radially inwardly to engage the at least one alignment feature protruding from the surface of the inner hub, wherein the inner tube is rotatably fixed with respect to the inner hub.

2. The surgical instrument of claim 1, wherein the reusable hub assembly further comprises:
    the outer hub comprising:
        an inner hub cavity;
        an outer tube receiving channel for releasably receiving the elongate outer tube;
        an outer tube retainer; and
        the inner hub being insertable into the inner hub cavity of the outer hub, the inner hub comprising an inner channel.

3. The surgical instrument of claim 2, wherein the outer tube retainer comprises an outer tube retainer fixed member disposed at a distal region of the outer hub, and an outer tube separate retaining member.

4. The surgical instrument of claim 3, wherein the outer tube retainer fixed member comprises a threaded region and the outer tube separate retaining member comprises one of:
    a removable cap; and
    a collet chuck.

5. The surgical instrument of claim 3, wherein the outer tube separate retaining member comprises a collet chuck including a nose cap and a collet comprising a flexible portion a ridged portion including a plurality of ridges extending radially outwardly from the flexible portion of the collet.

6. The surgical instrument of claim 3, wherein the outer tube separate retaining member comprises a collet chuck including a nose cap and a collet having a first end and a second end and defining a plurality of first open slots circumferentially disposed about the collet and extending from the first end and stopping short of the second end and a plurality of second open slots circumferentially disposed about the collet and each alternating with the plurality of first open slots and extending from the second end and stopping short of the first end.

7. The surgical instrument of claim 2, wherein the outer tube retainer comprises one of:
    a pin and groove system adapted to mate with a corresponding pin and groove system connection on a removable cap; and
    a snap-fit system adapted to mate with a corresponding snap-fit connection on a proximal end of the outer hub.

8. The surgical instrument of claim 2, wherein a cross-section of the outer tube receiving channel corresponds to an outer cross section of the elongate outer tube.

9. The surgical instrument of claim 8, wherein the outer tube receiving channel cross section comprises one of:
    an asymmetrical cross section; and
    a keyed symmetrical cross section, to orient an edgeform opening in the elongate outer tube with respect to a handpiece attached to the outer hub.

10. The surgical instrument of claim 2 further comprising one of a series of grooves and slots disposed on an inner surface of the outer hub for engagement with complementary tabs of the elongate outer tube.

11. The surgical instrument of claim 2, wherein the at least one alignment feature is radially and axially spaced from an opening of the inner channel relative to the longitudinal central axis.

12. The surgical instrument of claim 1, wherein the flange extends along the longitudinal central axis from the inner tube to extend along the conical frustum defined by the surface.

13. The surgical instrument of claim 1, wherein the at least one alignment feature extends rectilinearly along the surface and radially from the longitudinal central axis between the second diameter and the first diameter.

14. The surgical instrument of claim 1, wherein the disposable blade assembly further comprises:
    the elongate outer tube comprising:
        a distal region comprising an opening;
        an outer cross section for releasable engagement with the outer hub;
    the elongate inner tube rotatably disposed at least partially within the elongate outer tube, comprising:

a proximal end cross section, having a profile for releasable engagement with the inner channel of the inner hub;

a distal region comprising a cutting member, the cutting member being adjacent the elongate outer tube opening to permit resection of bodily tissue; and wherein the outer cross section of the elongate outer tube comprises an asymmetrical outer cross section, to orient the opening in the elongate outer tube with respect to a handpiece attached to the outer hub.

15. The surgical instrument of claim 14, wherein the surgical instrument further comprises an outer tube retainer comprising a collet chuck, and wherein the outer tube retainer comprises an outer tube retainer fixed member disposed at a distal region of the outer hub comprising a collet having a frustoconical shape and an outer tube separate retaining member comprising a nose cap.

16. The surgical instrument of claim 14, wherein the elongate outer tube further comprises one of:
    alignment tabs for engagement with corresponding slots in the outer hub; and
    slots for engagement with corresponding alignment tabs in the outer hub.

17. The surgical instrument of claim 14, wherein the elongate outer tube defines a swagable flange section being swagable on a proximal portion of the elongate outer tube and the outer hub includes an outer hub seal boss extending axially away from the outer hub and tapering in diameter from a first boss diameter to a second boss diameter smaller than the first boss diameter with increased axial distance away from the outer hub and toward the outer tube and configured to abut the elongate outer tube and radially deform and flare the swagable flange section and seal the proximal portion of the elongate outer tube to the outer hub.

18. The surgical instrument of claim 14, wherein the surgical instrument further comprises an outer tube retainer comprising an outer tube retainer fixed member disposed at a distal region of the outer hub including a threaded region and an outer tube separate retaining member comprising a removable cap having a threaded region to connect to the threaded region of the outer tube retainer fixed member.

19. The surgical instrument of claim 1, wherein the disposable blade assembly further comprises:
    the elongate outer tube comprising:
        a distal region comprising an opening;
        an outer cross section for releasable engagement with the outer hub;
    the elongate inner tube rotatably disposed at least partially within the elongate outer tube, comprising:
        a proximal end cross section, having a profile for releasable engagement with the inner channel;
        a distal region comprising a cutting member, the cutting member being adjacent the elongate outer tube opening to permit resection of bodily tissue; and
    wherein the outer cross section of the elongate outer tube comprises a keyed symmetrical cross section, to orient the opening in the elongate outer tube with respect to a handpiece attached to the outer hub.

* * * * *